(12) United States Patent
Hammack et al.

(10) Patent No.: US 8,177,741 B2
(45) Date of Patent: May 15, 2012

(54) CATHETER WITH SUPERELASTIC RETENTION DEVICE

(75) Inventors: Anthony D. Hammack, Bloomington, IN (US); Tracy Willis, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1215 days.

(21) Appl. No.: 11/402,596

(22) Filed: Apr. 12, 2006

(65) Prior Publication Data

US 2006/0229553 A1 Oct. 12, 2006

Related U.S. Application Data

(60) Provisional application No. 60/670,504, filed on Apr. 12, 2005.

(51) Int. Cl.
*A61M 29/00* (2006.01)

(52) U.S. Cl. ........ 604/96.01; 604/104; 604/524; 604/527; 604/264; 604/910; 604/915; 604/48

(58) Field of Classification Search ........ 604/6.16, 604/509, 95.04, 96.01, 97.01, 99.01, 99.02, 604/99.03, 264, 272, 910, 915, 48, 277–278, 604/527, 539, 907, 912, 104–107, 523
See application file for complete search history.

(56) References Cited

U.S. PATENT DOCUMENTS

| | | | | |
|---|---|---|---|---|
| 2,230,226 A * | 2/1941 | Auzin | ........ | 604/104 |
| 3,915,171 A * | 10/1975 | Shermeta | ........ | 604/101.05 |
| 4,043,338 A * | 8/1977 | Homm et al. | ........ | 604/105 |
| 4,921,484 A * | 5/1990 | Hillstead | ........ | 604/104 |
| 5,041,093 A * | 8/1991 | Chu | ........ | 604/104 |
| 5,318,530 A * | 6/1994 | Nelson, Jr. | ........ | 604/103.1 |
| 5,336,203 A * | 8/1994 | Goldhardt et al. | ........ | 604/247 |
| 5,456,251 A * | 10/1995 | Fiddian-Green | ........ | 600/345 |
| 5,842,971 A * | 12/1998 | Yoon | ........ | 600/101 |
| 5,868,708 A * | 2/1999 | Hart et al. | ........ | 604/104 |
| 5,891,113 A * | 4/1999 | Quinn | ........ | 604/526 |
| 5,906,606 A * | 5/1999 | Chee et al. | ........ | 604/527 |
| 5,911,702 A * | 6/1999 | Romley et al. | ........ | 604/509 |
| 6,033,359 A * | 3/2000 | Doi | ........ | 600/117 |
| 6,176,843 B1 * | 1/2001 | DiCaprio et al. | ........ | 604/99.03 |
| 6,569,150 B2 * | 5/2003 | Teague et al. | ........ | 604/524 |
| 6,589,208 B2 * | 7/2003 | Ewers et al. | ........ | 604/104 |
| 6,629,952 B1 * | 10/2003 | Chien et al. | ........ | 604/103.09 |
| 6,635,068 B1 * | 10/2003 | Dubrul et al. | ........ | 606/200 |
| 6,709,667 B1 | 3/2004 | Lowe et al. | | |
| 6,742,545 B2 * | 6/2004 | Fisher et al. | ........ | 138/137 |
| 6,763,833 B1 | 7/2004 | Khera et al. | | |
| 6,764,519 B2 | 7/2004 | Whitmore | | |
| 6,982,024 B2 * | 1/2006 | Shkolnik | ........ | 156/293 |
| 7,070,578 B2 * | 7/2006 | Leukanech et al. | ........ | 604/153 |
| 7,070,587 B2 * | 7/2006 | Meier et al. | ........ | 604/533 |
| 7,625,361 B2 * | 12/2009 | Suzuki et al. | ........ | 604/264 |
| 7,862,577 B2 * | 1/2011 | Gray et al. | ........ | 606/200 |
| 2004/0087905 A1 * | 5/2004 | Breznock et al. | ........ | 604/164.04 |
| 2005/0061771 A1 * | 3/2005 | Murphy | ........ | 216/17 |
| 2005/0090802 A1 * | 4/2005 | Connors et al. | ........ | 604/500 |
| 2005/0183729 A1 * | 8/2005 | Fischer, Jr. | ........ | 128/207.29 |
| 2006/0061771 A1 * | 3/2006 | Hill | ........ | 356/510 |
| 2006/0074308 A1 * | 4/2006 | Rafiee et al. | ........ | 600/435 |

* cited by examiner

*Primary Examiner* — Quynh-Nhu H Vu
(74) *Attorney, Agent, or Firm* — Brinks Hofer Gilson & Lione

(57) ABSTRACT

A retention device for use in a human or mammalian body includes superelastic wires that expand when they are released from a confined state. The retention device may have the outer form of a Foley catheter. One or more superelastic wires within the balloon of a Foley catheter help to insure retention within the body, such as within a urinary bladder.

14 Claims, 2 Drawing Sheets

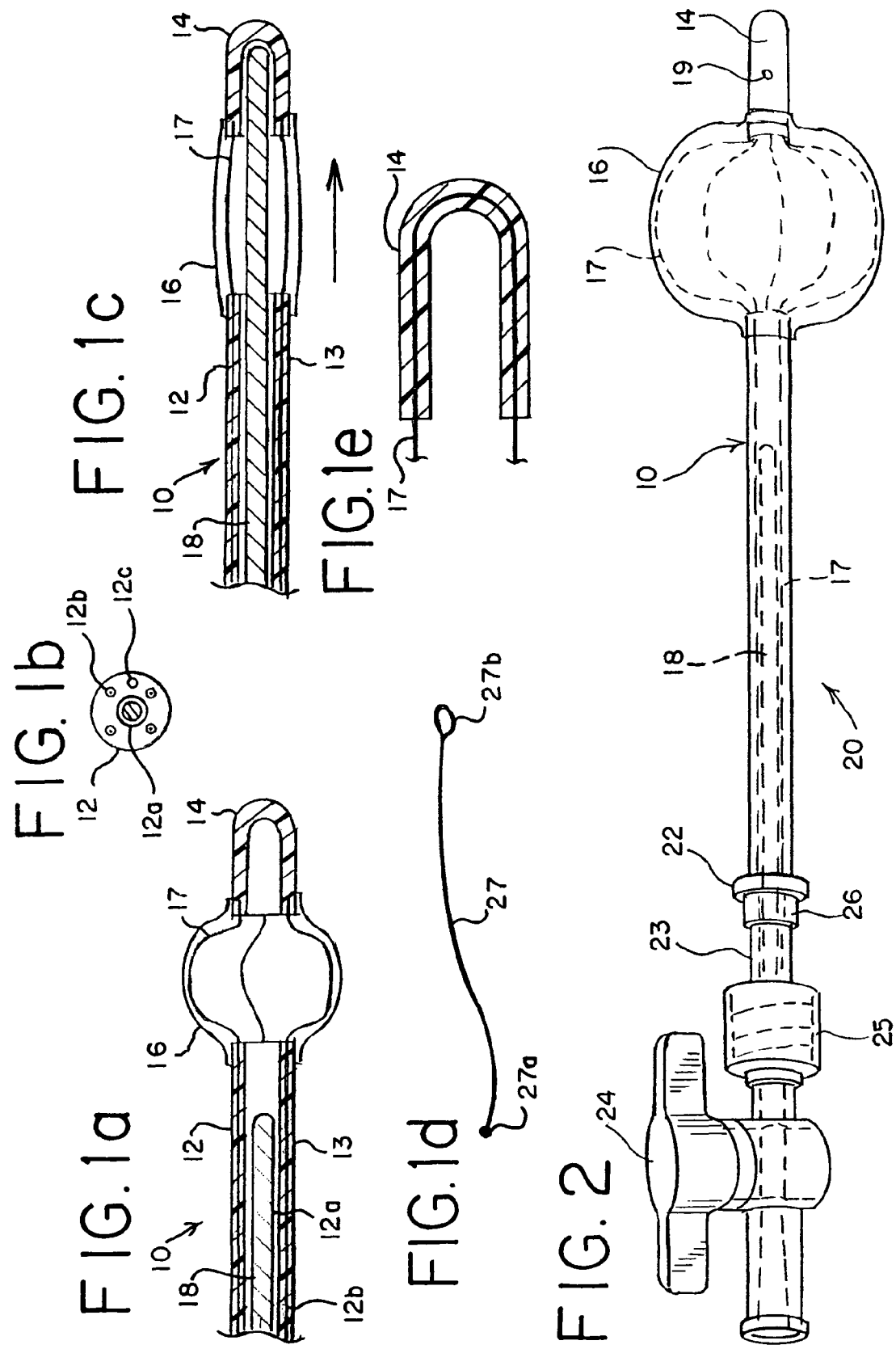

CATHETER WITH SUPERELASTIC RETENTION DEVICE

This application claims the benefit of the filing date under 35 U.S.C. §119(e) of Provisional U.S. patent application Ser. No. 60/670,504, filed on Apr. 12, 2005, which is hereby incorporated by reference in its entirety.

FIELD OF THE INVENTION

The technical field of the invention is that of medical devices, and in particular, medical devices for use in minimally-invasive surgical procedures.

BACKGROUND

Catheters and tubes are used in any number of ways during medical procedures. Foley catheters are well known devices, placed into a person to drain urine from the bladder. The Foley catheter is inserted, usually through the urethra, and a balloon, usually a silicone balloon, on the distal end is then inflated in order to secure the catheter within the bladder. Retention can be a problem, especially when the catheter is meant for placement for a longer period of time, such as several days. For instance, movement of the person can result in leakage of the saline or other solution used to inflate the balloon. The catheter may then be held only loosely, resulting in leakage, or the catheter could even escape its installation.

Feeding tubes, such as those resembling a Foley catheter or a Malecot catheter, are used in infants or other persons who are unable to suck or swallow food in a normal manner. In these instances, a surgeon makes an opening in the baby's or person's stomach, and a Malecot catheter or a Foley catheter may be placed into the opening, or even sutured into the opening. It is clearly very important that the feeding tube or catheter be securely placed in the opening.

There are many other applications for catheters and tubes, many of them placed percutaneously and requiring secure placement for at least several hours or days of time. One such demanding application for catheters or stents is their use in nephrostomy procedures. In these procedures, a physician will typically provide an opening into the kidney, for drainage or as part of a procedure for removing calculi. Malecot-type catheters are typically used, and it is critical for the patient's health and safety during the procedure that the catheter not be dislodged.

In virtually all applications, the device needs to be retained in the body of the patient to complete the procedure, or for a time period afterwards, such as for drainage of urine after a urinary procedure. In percutaneous procedures, the danger of infection and even sepsis requires complete control over the tube, whether it be a catheter, a stent or merely a tube. What is needed are better ways to retain such devices within the body, to allow physicians to complete a procedure, for the safety and well-being of the patient, or for convenience afterward.

BRIEF SUMMARY

One aspect of the invention is a retention device. The retention device includes a catheter having a proximal portion and a distal portion, a balloon mounted on the catheter between the proximal portion and the distal portion, the balloon connected to a fluid path in a proximal portion of the catheter, and at least one superelastic wire contained in the balloon and in at least one lumen within the catheter, the wires anchored to the distal portion, wherein the at least one wire assumes an expanded state when the balloon is inflated.

Another aspect of the invention is a retention device. The retention device includes a catheter having a proximal portion and a distal portion, and a balloon mounted on the distal portion, the balloon connected to an inflation lumen in the catheter and an inflation port on the proximal portion. The retention device also includes at least two superelastic wires contained in the balloon and in at least one lumen in the catheter, the wires anchored to the distal portion.

Another aspect of the invention is method for making a retention device. The method includes steps of extruding a longitudinal portion having at least a first lumen for drainage and a second lumen for inflation, and attaching a balloon to a distal end of the longitudinal portion. The method includes a step of attaching at least two superelastic wires to the distal end or to the balloon, and placing the wires through at least two lumens of the longitudinal portion, and attaching a connector to at least one of the drainage lumen and the inflation lumen to form at least one of a drainage port and an inflation port. The expanded shape allows the device to be more easily retained in the cavity into which it was inserted.

BRIEF DESCRIPTION OF THE DRAWINGS

FIGS. 1a and 1c are deployed (open) and collapsed views of an improved Foley catheter retention device according to the present invention;

FIG. 1b is a cross sectional view of the catheter of FIGS. 1a and 1c;

FIG. 1d is a plan view of a superelastic wire with retention features;

FIG. 1e is a cross-sectional view of an alternate distal end of a catheter;

FIG. 2 is a perspective view of a kit including the retention device;

DETAILED DESCRIPTION OF THE DRAWINGS AND THE PRESENTLY PREFERRED EMBODIMENTS

Figure 3:
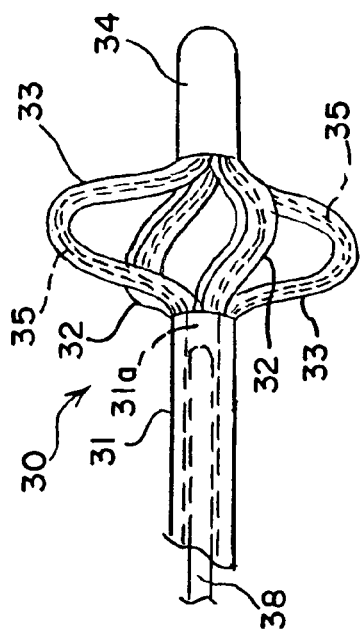
FIG. 3 is a perspective view of a Malecot catheter with an improved retention device.

There are many aspects of the invention, only a few of which are described herein. As discussed above, there is a great variety of catheters, tubes, and stents which benefit from the invention. Thus, embodiments of the invention may include Foley catheters, Foley feeding tubes, Rutner percutaneous balloon catheters, and so on.

One embodiment of the invention is depicted in FIGS. 1a and 1b, which depict an improved Foley catheter. FIG. 1a depicts the catheter inflated or deployed, while FIG. 1b depicts the catheter in a deflated state, ready for installation or removal. The improved Foley catheter 10 includes a catheter tube 12 having a central lumen 12a and one or more additional lumens 12b. The catheter includes a distal portion 12 connected via balloon 16. Non-central lumen 12c connects the inside of balloon 16 to an outside source of saline or other fluid for inflation. Lumen 12c may be routed through tube 12 or in a separate tube alongside tube 12, and is kept separate from central lumen (drainage line) 12a. Catheter 10 includes four superelastic wires 17, such as Nitinol wires. The wires extend from the proximal portion 13 through balloon 16 to the distal portion 14 of the catheter. The wires are normally retained within lumens 12b of tube 12.

As is well known, the catheter is inserted into a desired location, such as into a bladder of a patient. The balloon is inflated, typically by pumping in a small amount, several ml, of saline or other sterile solution. The balloon inflates and is then retained within the bladder of the patient. At the same time the balloon inflates, the superelastic wires 17 are partially pulled from lumens 12b and extend distally from catheter tube 12. The superelastic wires, no longer wholly retained within the tube, assume their relaxed position, as shown in FIG. 1a, helping to inflate the balloon with the bends which the wires have previously been "trained" to assume. The wires help to expand the balloon and keep the balloon inflated even if a small amount of leakage occurs from the balloon.

Another way to place the catheter is to insert an obturator 18 into the catheter, such that the distal tip of the obturator snugs against the distal tip 14 of the catheter, straightening the wires 17 and enabling the physician to place the catheter. The catheter may be thus placed percutaneously or endoscopically. When the physician is satisfied with the placement, the obturator can be removed, thus allowing the wires 17 to assume their relaxed, expanded state, and allowing the catheter to function.

When it is desired to remove the catheter, the obturator 18 may be used within central lumen 12a to collapse the balloon. The balloon may first be drained by applying a partial vacuum to the proximal end of lumen 12c. The vacuum device is then removed, and an obturator, such as a sterile stainless steel obturator, is then carefully inserted into central lumen 12a. Obturator 18 is then advanced in the direction of arrow A in the manner shown in FIG. 1b, causing the balloon to collapse and removing the retaining bends of the superelastic wires. The catheter is then ready for removal. An obturator made from a polymeric material, such as plastic or PTFE, made be used instead.

The wires are desirably anchored near at least one end or the other of the balloon. For example, as shown in FIG. 1d, a superelastic wire 27 may be formed with a retention feature 27a, 27b at one or both ends. When the catheter and balloon are formed, the wires may be molded into the distal end of the catheter or they may be molded into the catheter, located proximally of the balloon. The retention feature causes the wire to remain in place when the balloon is inflated. Instead of a portion with an enlarged diameter 27a, other features may be used, such as a tiny loop 27b. When molded into a distal end of the catheter, or into the catheter at a point proximal of the proximal end of the balloon, these retention features will anchor the superelastic wire while allowing the shape change of the wire to help inflate the balloon.

In another embodiment, shown in FIG. 1e, the wires may be looped around the distal end of the catheter. Thus two of the wires 17 in FIG. 2 may constitute a continuous loop around distal portion 14 of the catheter. The proximal ends of the wires of the loop extend into lumens 12b as shown in FIG. 1b. The distal end of the loop itself may be molded into the distal end of the catheter, anchoring the large loop to the distal end of the catheter in the same manner as the retention features discussed above, e.g., the small loop 27b.

The wires may be trained to assume the desired "bent" shape when they are partially pushed or pulled from lumens 12b. The wires 17 are preferably made of a superelastic or shape memory alloy, such as Nitinol, a nickel-titanium alloy. The wires may also be made from other shape memory metals, such as alloys of Cu—Zn—Al or Cu—Al—Ni. In order to keep the size of the catheter and the diameter of the tube narrow, very thin wires are preferred, such as wires having a diameter of about 0.0025 inches (about 0.063 mm). Round wires are preferred, but wires of any shape may be used, including rectangular wire, square wire, wedge or "pie-shaped" wire, flat wire and triangular wire. Of course, the wires must have sufficient diameter to exert an adequate force upon the balloon or other device, in order to resist deflation and to assist in retaining the balloon or other device in its desired location within the patient.

As is well known in the art, the wires may be formed into a desired shape and heat treated or "trained" into that shape by heating to a certain temperature for a certain length of time. Typically, temperatures in the range of 500-540° C. and times from 1-5 minutes are used. Other temperatures and times may also be used. Shape-memory or superelastic materials are heat treated or annealed from a weak (martinsite) structure to a strong (austenite) structure. The alloys are weak and deformable in the martinsitic state, which is thus useful for forming the loops. After transformation to the strong or austenitic state, they exhibit a superelastic property so long as the material remains above a transformation temperature, at which temperature it will revert to the martensitic state. The transformation temperature is desirably a low temperature, well below the temperature of a human body, and preferably below room temperature, which is at least about 20-25° C. The transformation temperature of the wires is thus selected to be well below the operating temperature of the catheter or other device to be retained within the body, thus keeping the wire in a superelastic state. In this state, the wires advantageously return to their original, unstressed shape when deforming stresses are removed. The superelastic wire alloy also increasingly resists deformation as the stress load is increased. Thus, when a superelastic wire is collapsed and placed into the lumen 12b, the wire is placed in a state of stress. When the wires are deployed, the stresses are removed, and the wires return to the desired bent shape.

The bends are formed by shaping the wires into the desired shape at room temperature or below, preferably with a cold mandrel, and then annealing the properly-shaped wires at the proper annealing temperature for a time sufficient for the transformation to a superelastic state. In one example, a bent wire is formed from 0.11 mm diameter (about 0.0043 inches) Ni—Ti Nitinol wire and is annealed at 990° F. (about 530° C.) for about 10 minutes. The time and temperature for annealing will vary with the alloy selected and with the diameter (thickness) of the wire. The wires themselves, not merely the annealing oven, must remain at the desired temperature for the proper length of time for the annealing or heat-treatment to be complete. Proper annealing is very important for the wires to remain kink-free during deployment and operation of the catheter or other device. If kinks form for any reason, it may be difficult to deploy (expand) or retract the catheter or other device. The bends are desirably formed before the annealing operation, as discussed above, including all wires or bends for a given catheter or other device.

The improved Foley catheter described above may be used as part of a system. FIG. 2 depicts a kit 20 or system that includes a Foley catheter 10, connector 22, tubing 23, and stopcock 24 with connectors 25. A one-way check valve 26 may also be used to insure only one-way flow through central lumen 12a. Catheter 10 includes balloon 16 (shown inflated), superelastic wires 17 in their relaxed state, and distal portion 14. Catheter 10 may also include one or more orifices 19 for draining the bladder into which the catheter is placed. Other applications for improved Foley-type instruments may include percutaneous suprapubic balloon catheters, urethrogram catheters, and gastrostomy feeding tubes.

Other embodiments may include Malecots. As depicted in FIG. 3, an improved Malecot catheter 30 includes a catheter tube 31 one or more orifices 32 for drainage, and a distal end 34 connected to tube 32 by "wings" 33. Wings 33 include a superelastic wire 35 as described above, embedded within or on an inner surface of the wings, or at least one wing. Malecot catheter 30 may also include an obturator 38 for holding the wings of the catheter in place until deployment is desired. The obturator is assembled in central lumen 31a of the catheter, with the distal tip of obturator 38 just inside distal end 34 of the catheter. The Malecot is placed into the desired area, with the obturator held tightly to keep the wings in place. When the obturator is removed, the superelastic wires assume their relaxed, bent shape, the wings deploy outward, and the Malecot is held in place. When the Malecot is to be removed, the process is reversed, again using an obturator or similar instrument to "fold" the wings and enable removal.

Figure 4:
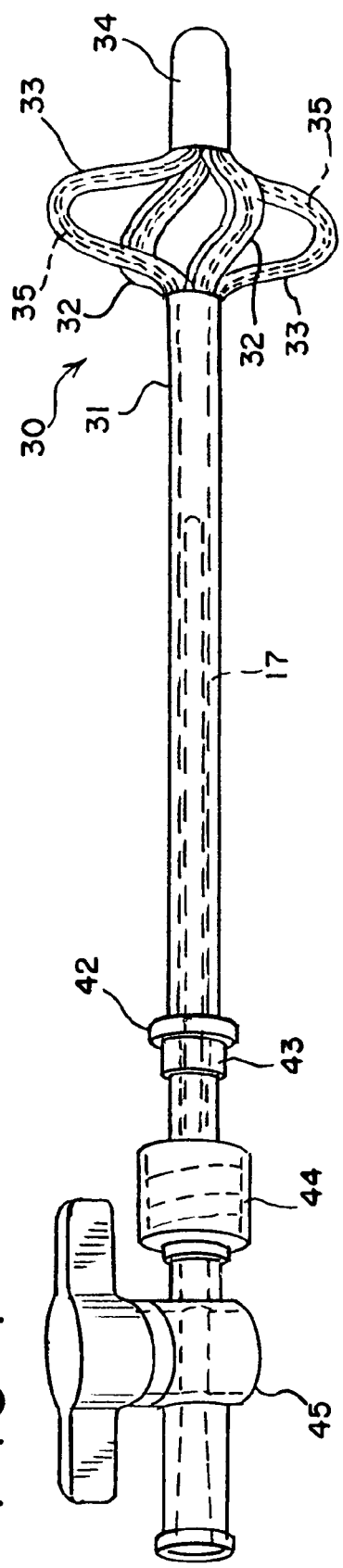
FIG. 4 depicts a kit using the improved retention device of FIG. 3.

Malecots may be part of a kit or system, as depicted in FIG. 4. In this example, after Malecot 30 is deployed and the obturator removed, tube 31 may be connected via connector 42 to a check valve 43 as desired, and via connector 44 to a valve 45. Tube 31 may include superelastic wires 17. In this manner, a Malecot-type device may be used, as mentioned above, for drainage or for feeding. Malecot-type devices with improved retention capabilities may also be used for nephrostomy procedures, percutaneous procedures, and other medical procedures where improved retention is desired.

It is therefore intended that the foregoing detailed description be regarded as illustrative rather than limiting, and that it be understood that it is the following claims, including all equivalents, that are intended to define the spirit and scope of this invention.

What is claimed is:

1. A retention device, comprising:
    a catheter having an outer circumferential surface, a proximal portion and a distal portion and a central lumen defined therethrough;
    a balloon mounted on the catheter between the proximal portion and the distal portion, the balloon connected to a fluid path in a proximal portion of the catheter;
    at least one superelastic wire contained in the balloon and in at least one lumen within the catheter, wherein the at least one wire extends from the proximal portion through the balloon to the distal portion, wherein at least one end of the wire comprises a retention feature that is anchored to a portion of the catheter, wherein at least a portion of the at least one wire is biased into a radially expanded configuration outside of the outer circumferential surface of the catheter to assist the inflation of the balloon and assist in maintaining the balloon in the expanded state; and
    an obturator, wherein the catheter is configured to receive a distal tip of the obturator pressed against a distal tip of the catheter within the distal portion, wherein the force applied to the distal tip of the catheter straightens the at least one wire from the radially expanded configuration allowing the balloon to maintain a collapsed configuration,
    wherein when the balloon is inflated, the at least one superelastic wire is partially pulled from the at least one lumen and extends distally from the catheter and is not wholly retained within the catheter.

2. The retention device of claim 1, wherein the device comprises at least two superelastic wires and the catheter comprises a lumen for each wire, wherein the two wires are looped together around an end of the distal portion of the catheter.

3. The retention device of claim 1, further comprising an inflation check valve.

4. The retention device of claim 1, further comprising a stopcock connected to the central lumen.

5. The retention device of claim 1, wherein the fluid path comprises a non-central lumen in the catheter.

6. The retention device of claim 1, wherein the obturator is made from a polymeric material.

7. The retention device of claim 1, wherein at least one superelastic wire is anchored to the distal portion of the catheter.

8. A retention device, comprising:
    a catheter having an outer circumferential surface, a proximal portion and a distal portion and a central lumen defined therethrough;
    a balloon mounted on the distal portion, the balloon connected to an inflation lumen in the catheter and an inflation port on the proximal portion; and
    at least two superelastic wires contained in the balloon and in at least one lumen in the catheter, the wires anchored to the distal portion, wherein a portion of each of the wires are biased to an arcuate configuration extending radially outside of the circumferential surface of the catheter, with the biased portion of each wire in registry with the balloon, such that the wires tend to urge expansion of the balloon,
    wherein when the balloon is inflated, the at least two superelastic wires are partially pulled from the at least one lumen and extends distally from the catheter and are not wholly retained within the catheter.

9. The retention device of claim 8, wherein the wires are flat or wedge-shaped.

10. The retention device of claim 8, further comprising at least one of an obturator, a connecting tube, and a stopcock for use with the retention device.

11. The retention device of claim 8, wherein the wires have a transformation temperature below room temperature.

12. The retention device of claim 8, wherein at least one superelastic wire has a retention feature providing the anchor between the wires and the catheter.

13. The retention device of claim 8, wherein two wires of the at least two wires are connected together at distal ends thereof and define a loop disposed around a distal end of the distal portion of the catheter, with the loop being molded into the distal end of the catheter.

14. The retention device of claim 8, further comprising an obturator insertable into the central lumen of the catheter, wherein a distal tip of the obturator is configured to be pressed against the distal portion of the catheter which pulls the wires toward the distal portion and causes the wires to elongate to a relatively straight configuration from their normal arcuate configuration.

* * * * *